United States Patent [19]

Mori

[11] Patent Number: 6,017,552

[45] Date of Patent: *Jan. 25, 2000

[54] SOLID COSMETIC COMPOSITION

[75] Inventor: Tamotsu Mori, Yasu-gun, Japan

[73] Assignee: The Procter & Gamble Company, Cincinnati, Ohio

[ * ] Notice: This patent is subject to a terminal disclaimer.

[21] Appl. No.: 09/237,720

[22] Filed: Jan. 26, 1999

Related U.S. Application Data

[63] Continuation of application No. 08/849,703, Jun. 6, 1997, which is a continuation of application No. PCT/US95/01848, Feb. 14, 1995.

[30] Foreign Application Priority Data

Dec. 9, 1994 [JP] Japan ..................................... 6-306291

[51] Int. Cl.[7] ...................................................... A61K 7/48
[52] U.S. Cl. .......................... 424/401; 424/69; 424/78.02; 514/844
[58] Field of Search .......................... 424/401, 69, 78.02; 514/844

[56] References Cited

U.S. PATENT DOCUMENTS

| 4,837,011 | 6/1989 | Macchio et al. | 424/69 |
| 5,030,446 | 7/1991 | Russ et al. | 424/63 |
| 5,234,682 | 8/1993 | Macchio et al. | 424/69 |
| 5,288,481 | 2/1994 | Ounanian et al. | 424/63 |

FOREIGN PATENT DOCUMENTS

| 0529396A1 | 3/1993 | European Pat. Off. . |
| 4-117315A | 4/1992 | Japan . |
| 4-187612A | 7/1992 | Japan . |

OTHER PUBLICATIONS

Soap/Cosmetics/Chemical Specialties, vol. 62, No. 2, p. 97, "New Chemicals for Specialties", See paragraph on "Silica, Titanium Dioxide Powders", Feb. 1986.

*Primary Examiner*—Jyothsna Venkat
*Attorney, Agent, or Firm*—T. David Reed; Dara M. Kendall; Darryl C. Little

[57] ABSTRACT

The present invention relates to solid cosmetic composition which contains a powder with high oil absorbency and can suppress oil shining.

12 Claims, No Drawings

SOLID COSMETIC COMPOSITION

CROSS-REFERENCE TO RELATED APPLICATION

This application is a continuation of U.S. application Ser. No. 08/849,703, filed Jun. 6, 1997, which is the §371 application of PCT/US95/01848, filed Feb. 14, 1995.

TECHNICAL FIELD

The present invention relates to a solid cosmetic composition which contains a powder with high oil absorbency and can suppress oil shining and the like.

CONVENTIONAL TECHNOLOGY

It has been considered that one reason of wear-off of make-up as oil shining is due to generation of sebum at the T-zone. It is thought that wear-off of make-up such as oil shining is caused by generation of sebum from the skin over time after cosmetic composition is applied, which sebum adds to the non-volatile oil contained in the cosmetic composition, resulting in overly wetting the powder of the cosmetic composition.

Japanese Patent laid-open H4-117315 and H4-187612 disclose cosmetic compositions which can prevent wear-off of make-up, comprising oil absorbing powders such as polymer beads.

OBJECT OF THE INVENTION

However, these cosmetic compositions could not provide sufficient suppression of oil shining, and also could not provide a natural finished appearance.

The object of the present invention is to provide a cosmetic composition which can suppress oil shining without affecting a natural finished appearance, and can also provide moisturizing effect to non-aqueous cosmetic compositions as necessary.

DETAIL DESCRIPTION OF THE INVENTION

The cosmetic composition of the first aspect of the present invention is characterized in comprising 0.1–10 wt % to the entire composition spherical silica having an average particle size of 3–16 $\mu$m wherein said spherical silica is adsorped with moisturizing agent.

The cosmetic composition of the second aspect of the present invention is characterized in comprising (1) 40–99 wt % of a powder component and (2) 0.1–60 wt % of a binder base; and (1) powder component further comprises (a) a spherical silica having an average particle size of 3–16 $\mu$m and (b) an agglomerate having a particle size of 100–2000 $\mu$m made of primary particles of spherical acrylate cross-linked copolymer having an average particle size of no more than 1 $\mu$m; wherein said (a) spherical silica and said (b) spherical acrylate cross-linked-copolymer agglomerate is comprised at a weight ratio (a:b) of 1:9–9:1, and the total of said (a) spherical silica and said (b) spherical acrylate cross-linked-copolymer agglomerate is 0.1–10 wt % to the entire composition.

Hereinafter, common components of the first and second aspects of the present invention will be described collectively as the "present invention".

The spherical silica used in the present invention is preferably a "Silicic Anhydride" as specified in The Japanese Standards of Cosmetic Ingredients. Those which have a spherical shape are used as they have good lubricating properties.

The spherical silica used in the present invention has an average particle size of 3–16 $\mu$m. If the particle size is too small, the oil absorbency will be too high that more than necessary oil is absorbed and dryness is caused. Lubricity will also deteriorate, and undesirable pulling feeling will increase.

If the particle size is too large, the oil absorbency will be too low that not enough oil can be absorbed. Also unevenness of color would appear and molding becomes difficult.

The spherical silica used in the present invention is preferably a spherical porous silica having an oil absorbency of about 60–500 ml/100 g.

In the first aspect of the present invention, said spherical silica adsorped with moisturizing agent is comprised at a level of 0.1–10 wt % to the entire composition. The amount of moisturizing agent adsorped is preferably no more than the weight of the spherical silica. At this level, good adsorption of the moisturizing agent as well as good oil absorbency can be obtained.

The spherical silica adsorped with moisturizing agent is comprised at an amount of 0.1–10 wt % of the entire composition. If the amount is too small, sufficient oil absorbency and oil shining suppression cannot be obtained, and if the amount is too large, dryness and unevenness of color appears.

In the second aspect of the present invention, spherical silica and spherical acrylate cross-linked copolymer agglomerates are comprised as essential components in a solid cosmetic composition comprising 40–99 wt % powder component and 0.1–60 wt % binder base.

The spherical acrylate cross-linked copolymer agglomerates used in the second aspect of the present invention have a cross-linked structure of methacrylate polymers, and are made of tertiary agglomerates consisting of porous spherical fine particles. These agglomerates make capillary-like pores. The primary particles of these spherical acrylate cross-linked copolymers have an average particle size of not more than 1 $\mu$m. If the average particle size is larger than this, the desired agglomerates could not be made, and thus sufficient oil absorbency and oil shining suppression could not be obtained.

The spherical acrylate cross-linked copolymer agglomerates used in the second aspect of the present invention have a particle size of 100–2000 $\mu$m as the agglomerate. By taking this particle size, superior oil absorbency and in-use feeling can be obtained. An example of those having this characteristic is trade name POLYTRAP Q5-6603 Acrylate Copolymer (provided by Toray Dow Corning Silicone).

In the second aspect of the present invention, said spherical silica and spherical acrylate cross-linked copolymer agglomerate as described above are comprised at a weight ratio of 1:9–9:1. In this ratio, a cosmetic composition having preferable oil absorbency and oil shining suppression can be obtained.

In the second aspect of the present invention, the total of said spherical silica and said spherical acrylate cross-linked-copolymer agglomerate is 0.1–10 wt % to the entire composition. If the amount is too small, sufficient oil absorbency and oil shining prevention effect cannot be obtained, while, if the amount is too high, it causes dryness and unevenness of color.

In the second aspect of the present invention, a moisturizing agent can be adsorped to said spherical silica or spherical copolymer agglomerate to enhance moisturizing effect. The amount of moisturizing agent to be adsorped is preferably not more than the weight of the spherical silica. At this level, good adsorption of the moisturizing agent can be obtained while having sufficient oil absorbency.

Examples of moisturizing agents which can be used in the present invention are polyhydric alcohols, solutions of mucopolysaccharides such as sodium hyaluronate solution, protein and amino acid solutions such as collagen and elastin. Most preferred are polyhydric alcohols.

When glycerin is adsorped to the spherical silica as a polyhydric alcohol moisturizing agent, it is preferable that the weight ratio of spherical silica to glycerin is within the range of 95:5–50:50. If the ratio is less than 95:5, sufficient moisturizing effect cannot be seen, while if it is more than 50:50, manufacturing can become difficult.

When polyhydric alcohol is adsorped to spherical silica, it is preferable that a solution made of 100 weight parts of polyhydric alcohol and 10–50 weight parts of water is adsorped to spherical silica, and then the water is removed by drying.

The spherical silica in the present invention can be hydrophobically modified with silicones such as methylhydrogen polysiloxane. When moisturizing agents such as polyhydric alcohols are adsorped to spherical silica, such hydrophobic modification treatment is preferably done after adsorption of moisturizing agent. Such silicone treatment can be done by adding the treating agent, stirring, and then heating, preferably at about 130° C. This is to prevent decoloring of the adsorped moisturizing agent.

The cosmetic composition of the present invention can further comprise various components which are generally contained in a cosmetic composition. The cosmetic composition according to the second aspect of the present invention comprises 0.1–60 wt % of binder base, and in case of press-molded solid cosmetic compositions, 1–30 wt %, preferable 5–20 wt % of lipophilic material in the binder base. Lipophilic material is usually comprised in the cosmetic composition as a portion of the binder base. Hereinafter, optional components such as lipophilic material, pigments, and others are described.

Lipophilic Material

The lipophilic material used in the present invention can selected from the group consisting from solid lipophilic material, liquid oil, oil gelling agent, and mixtures thereof. These components are selected by the one skilled in the art according to the desired cosmetic composition to be make. Preferably, for cosmetic compositions such as foundations, eye shadows, and blushers, the mixture of solid lipophilic material, liquid oil, and oil gelling agent is included.

Solid Lipophilic Material

The solid lipophilic material act as a solidifying agent in the cosmetic composition. It can assist in the formation of the solid structure of the composition. The solid is a low-melting organic compound or mixture of high molecular weight substances, and is solid or paste at room temperature. The solids can be waxes, hydrocarbons, fatty acids, fatty alcohols, natural fats, or esters, but not limited thereof.

Natural, mineral synthetic waxes can be used herein. Non-limiting examples of natural waxes of animal origin are beeswax, spermaceti, lanolin, shellac wax, or of vegetable origin, such as carnauba, candelilla, bay berry, sugarcane wax, and of mineral origin, such as ceresin, montan, paraffin, microcrystalline, vaseline, petroleum and petrolatum wax. Non-limiting examples of synthetic waxes are polyol ether-esters such as carbowax and hydrocarbon-type waxes, silicone waxes and polyethylene was. Synthetic triglycerides in wax form such as esters of linear fatty acids are also useful. The most preferred waxes are ceresin, lanolin, microcrystalline, carnauba, beeswax, and paraffin waxes.

The fatty acids used herein can be saturated, unsaturated, linear, or branched. Non-limiting examples are lauric, myristic, palmitic, stearic and behenic acids.

Non-limiting examples of fatty alcohols used herein are octyl, decyl, lauryl, myristyl, cetyl, stearyl, and behenyl alcohols.

Non-limiting examples of the natural fats useful herein are palm oil, Japan wax, hydrogenated vegetable oil, hydrogenated castor oil, and cholesterol.

Non-limiting example of the esters useful herein are myristyl myristrate, myristyl palmitate, myristyl stearate, cetyl palmitate, cetyl stearate, cetyl lactate, stearyl lactate, cholesterol stearate, cholesterol oleate, cholesterol palmitate, cholesterol laurate, cholesterol myristate, cholesterol lineolate, and cholesterol ricinoleate.

Liquid Oils

The liquid acts as emollients, and imparts tackiness, and drag properties to the cosmetic. Liquid oils are material that freely flow at room temperature. Liquid oils can also be volatile. Said liquid oils can be hydrocarbon oils, natural oils, fatty alcohols, fatty acid esters, and silicone oils, but not limited thereof.

Non-limiting examples of the hydrocarbons useful in the present invention are liquid paraffin, squalane, liquid petrolatum, mineral oil, and liquid polybutenes.

The natural oils used herein typically are mixtures of saturated and unsaturated fatty acids. Non-limiting examples of natural oils derived from plants include almond oil, olive oil, sesame oil, safflower oil, avocado oil, cottonseed oil, jojoba oil, castor bean oil, castor oil, rapeseed oil, soybean oil, palm kernel oil, and coconut oil. Non-limiting examples of natural oils derived from animal sources are mink oil and egg yolk oil.

Non-limiting examples of fatty alcohols useful in the present invention are isostearyl alcohol, lanolin alcohol, oleyl alcohol, hexadecyl alcohol, octyldodecanol alcohol, linoleyl alcohol, linolenyl alcohol, and arachidyl alcohol.

Fatty acids useful in the present invention can be natural or synthetic, saturated, unsaturated, linear, or branched. Non-limiting examples of fatty acids useful in the present invention are adipic, caprylic, capric, isostearic, linoleic, ricinoleic, oleic, elaidic and erucic acids.

Non-limiting examples of the fatty acid esters useful in the present invention are cetyl ricinoleate, cetyl oleate, cetyl octanoate, cetyl acetate, glyceryl trioctanoate, isopropyl lanolate, isopropyl linoleate, isopropyl myristate, isopropyl palmitate, isopropyl oleate, isopropyl stearate, ethyl lactate, ethyl glutamate, ethyl laurate, ethyl linoleate, ethyl methacrylate, ethyl myristate, ethyl palmitate, diisopropyl adipate, octyl dodecyl myristate, octyl palmitate, octyl isopelargonate, octyl dodecyl lactate, tridecyl isononanoate, isotridecyl isononanoate, hexadecyl stearate, oleyl oleate, isononyl isononanoate, isostearyl myristate, dipentaerythrytol ester, neopentyl glycol diosctanoate, and di(capryl/capric acid) propylene glycol. Other suitable ester include triglycerides such as caprylic triglycerides, capric triglyceride, isostearic triglyceride, adipic triglyceride, and cholesterol derivatives such as cholesteryl oleate.

Non-volatile and volatile, straight, branched, and cyclic silicone oils such as dimethicone, phenyl dimethicones, and cyclomethiocones are also useful.

Oil Gelling Agents

The oil gelling agents are included for gelatinizing or viscosity controlling of the formulation. Non-limiting examples of oil gelling agents useful in the present invention are condensation products of benzaldehydes and polyhydric alcohols having at least 5 bases such as dibenzylidene xylitol, paratribenzylidene sorbitol, metal soaps such as calcium stearate, calcium palmitate, lithium salt of 2-ethyl hexane, aluminium salt of 1,2,hydroxystearate, amide ester, and amide derivatives of N-acylamino acids such as lauroyl glutamate dibutylamide, lauroyl glutamate stearamide, dicapropyl lysine lauroylamide, dicaproyl lysine lauroylamine salt, dicapropyl lysine lauryl ester, dicaproyl lysine lauroyl phenylalanine laurylamide; dextrine fatty acid esters, and 1,2-hydroxystearic acid.

Pigments

Non-limiting examples of pigments useful in the present invention are talc, mica, clay, kaolin, zinc oxide, nylon powder, ultramarine, pearl pigments (bismuth oxychloride, guanine), iron oxide, titanium oxide, titanated mica, calcium carbonate, tar pigments, and other organic pigments. Pigments which are surface treated with silicones and its derivatives, metal soaps, fluorine compounds and its derivatives, lecithin and its derivative, amino acids and its salts, etc. can also be used.

The pigments can also be dispersed in an oily medium such as those disclosed above under liquid oils prior to use in the making process. Pigments can be purchased pre-dispersed in an oily medium like castor oil, or as dry powders which subsequently are dispersed in a chose medium by the formulator.

Other Optional Components

The compositions made by the process of the present invention can optionally contain components in addition to those already disclosed herein.

Optional components include antioxidants, preservatives, antiinflauuatory agents, astringents, pH buffers, perfumes, ultraviolet and infrared screening agents, nonionic surfactants such as fatty acid esters and polyoxyalkylene fatty acid esters, amphoteric and anionic surfactants such as lecithins and phosphates, vitamins, and skin conditioning agents.

Antioxidants and preservatives can be, and usually will be formulated in the composition of the present invention to make products attractive to the consumer. Useful antioxidants and preservatives are tocopherol, dibutylhydroxy toluene, methylparaben, and propylparaben. These components are typically present at levels not more than 1 wt % respectively.

Useful skin condition agents are beta-glycyrrhetic acid and its derivatives, vegetation extracts, allantoin, collagen, and extract and treated elastin fibers.

Effect of the Invention

As the solid cosmetic composition of the present invention comprise powder with high oil absorbency, it absorbs the sebum of the T-zone, and thus can sufficiently suppress wear-off of make-up and oil shining due to sebum.

Further, the solid cosmetic composition of the present invention uses spherical powders, and thus has superior in-use feeling without affecting natural finished appearance.

Further, the solid cosmetic composition of the present invention, when said spherical silica is adsorped with moisturizing agent, can show superior moisturizing effect, particularly in non-aqueous cosmetic compositions.

EXAMPLES

The following examples illustrate the compositions of the present invention, but are not intended to be limiting thereof. All percentages and ratios are based on weight unless otherwise specified.

Powder Foundation

The cosmetic compositions having compositions as shown in Table 1 were prepared as follows: First, the components of Phase A were mixed in a Henshel Mixer and then ground and dispersed. Next, the components of Phase B were heated (85° C.) under stirring in a stainless kettle and dissolved homogeneously. The mixture of Phase B is added into Phase A, mixed, and ground. The obtained mixture is transferred into a tray, press-molded, and cosmetic compositions suitable for a powder foundation was obtained.

The silicone-treated spherical silica was made by surface treating 2 wt % methylhydrogen polysiloxane silica. The spherical silica used here was a silicic anhydride having an average particle size of 5 $\mu$m. The oil absorbency of the silicone-treated spherical silica was 350 ml/100 g, surface area was 900 $m^2$/g, and the pore size was 250 A.

The surface-treated glycerin-adsorped spherical silica was made by mixing and adsorbing 40 wt % glycerin to 60 wt % of silicic anhydride as used above to make silicone-treated spherical silica, and then surface treated with 2 wt % of methylhydrogen polysiloxane. The oil absorbency of the silicone-treated spherical silica was 150 ml/100 g, surface area was 900 $m^2$/g, and the pore size was 60 A.

The spherical acrylate copolymer corresponds to the spherical acrylate cross-linked copolymer agglomerates as described above. A material available in the market with trade name POLYTRAP Q5-6603 Acrylate Copolymer (provided by Toray Dow Corning Silicon) was used. The zirconium oxide-treated nylon powder titanium oxide is a complex powder wherein fine-particle zirconium oxide is attached to the surface of spherical nylon powder encompassing fine particle titanium oxide. It is made by 63 wt % nylon powder, 30 wt % zirconium oxide, and 7 wt % titanium oxide. The average particle size is 5 $\mu$m.

Silicone-treated talc, silicone-treated titanium oxide, silicone-treated sericite, silicon-treated mica, and silicone-treated plate-like titanium oxide are all surface treated with 2 wt % of methylhydrogen polysiloxane, respectively.

Silicone treatment can be made by wither dry method process or wet method process. Oil absorbency is measured according to Japanese Industrial Standard K-5101-19. "Oil Absorbency" wherein linseed oil is replaced with liquid paraffin.

TABLE 1

| | Amount (%) | | |
| --- | --- | --- | --- |
| Component | Example 1 | Example 2 | parative Example |
| Phase A | | | |
| Silicone-treated talc | 8.9 | 8.9 | 8.9 |
| Silicone-treated titanium oxide | 10.5 | 10.5 | 10.5 |
| Silicone-treated sericite | 18.0 | 18.0 | 18.0 |
| Silicone-treated mica | 20.0 | 21.5 | 26.5 |

TABLE 1-continued

| Component | Amount (%) | | |
|---|---|---|---|
| | Example 1 | Example 2 | Comparative Example |
| Silicone-treated plate-like titanium oxide | 11.0 | 11.0 | 11.0 |
| Nylon powder | 5.0 | 5.0 | 5.0 |
| Zirconium oxide-treated nylon powder titanium oxide | 4.3 | 4.3 | 4.3 |
| Silicone-treated glycerin-adsorped spherical silica | 1.5 | — | — |
| Silicone-treated spherical silica | 3.0 | 3.0 | — |
| Spherical acrylate copolymer | 2.0 | 2.0 | — |
| Pigments | 1.8 | 1.8 | 1.8 |
| Phase B | | | |
| Paraben and antioxidants | 0.15 | 0.15 | 0.15 |
| Silicone oil | 7.35 | 7.35 | 7.35 |
| Squalane | 2.5 | 2.5 | 2.5 |
| Purified lanolin | 1.0 | 1.0 | 1.0 |
| Octyl methoxy cinnamate | 3.0 | 3.0 | 3.0 |
| Absorbency (ml/100 g) | 40.0 | 40.0 | 36.0 |

As shown in Table 1, the powder foundations of Example 1 and Example 2 according to the present invention showed higher oil absorbency than Comparative Example 1.

A sensory test was conducted using 132 panelists for the powder foundations of Examples 1 and 2. As a result, those panelists who answered that they felt moisturizing effect were 81 for Example 1, and 73 for Example 2.

Next, powder foundations having compositions as shown in Table 2 were prepared in the same manner as described above.

TABLE 2

| Component | Amount (%) | |
|---|---|---|
| | Example 3 | Comparative Example 2 |
| Phase A | | |
| Silicone-treated talc | 70.0 | 77.0 |
| Silicone-treated titanium oxide | 3.0 | 3.0 |
| Silicone-treated mica | 15.0 | 15.0 |
| Silicone-treated glycerin-adsorped spherical silica | 1.0 | — |
| Silicone-treated spherical silica | 3.0 | — |
| Spherical acrylate copolymer | 3.0 | — |
| Antioxidant Paraben | 0.15 | 0.15 |
| Pigments | 0.25 | 0.25 |
| Phase B | | |
| Silicone oil | 2.6 | 2.6 |
| Squalane | 2.0 | 2.0 |
| Absorbency (ml/100 g) | 60.0 | 51.0 |

As is shown in Table 2, Example 3 according to the present invention showed higher oil absorbency than Comparative Example 2.

Loose Face Powder

Loose face powders of Example 4 and Comparative Example 3 having formulations as shown in Table 3 were prepared in the same manner as described above.

TABLE 3

| Component | Amount (%) | |
|---|---|---|
| | Example 4 | Comparative Example 3 |
| Phase A | | |
| Silicone-treated talc | 74.2 | 81.2 |
| Silicone-treated titanium oxide | 3.0 | 3.0 |
| Silicone-treated mica | 15.0 | 15.0 |
| Silicone-treated glycerin-adsorped spherical silica | 2.0 | — |
| Silicone-treated spherical silica | 2.0 | — |
| Spherical acrylate copolymer | 3.0 | — |
| Pigments | 0.65 | 0.65 |
| Phase B | | |
| Antioxidant Paraben | 0.15 | 0.15 |
| Absorbency (ml/100 g) | 66.0 | 58.0 |

As is shown in Table 3, Example 4 according to the present invention showed higher oil absorbency than Comparative Example 3.

Oiliness Foundation

The cosmetic compositions having compositions as shown in Table 4 were prepared as follows: First, the components of Phase A were mixed in a Henshel mixer and then ground and dispersed. Next, the components of Phase B were heated (85° C.) under stirring and dissolved homogeneously. The obtained mixture of Phase A is added into the mixture of Phase B under stirring, and then further stirred in a Daysolver. The obtained mixture was poured into a tray at 85° C., cooled to solidify, and cosmetic compositions suitable for an oiliness foundation was obtained.

TABLE 4

| Component | Amount (%) | |
|---|---|---|
| | Example 5 | Comparative Example 4 |
| Phase A | | |
| Silicone-treated talc | 19.5 | 28.0 |
| Silicone-treated mica | 10.0 | 10.0 |
| Silicone-treated titanium oxide | 13.0 | 13.0 |
| Silicone-treated glycerin-adsorped spherical silica | 2.5 | — |
| Silicone-treated spherical silica | 2.0 | — |
| Spherical acrylate copolymer | 4.0 | — |
| Pigments | 3.0 | 3.0 |
| Phase B | | |
| Liquid paraffin | 14.95 | 14.95 |
| Isoproply palmitate | 13.0 | 13.0 |
| Lanolin alcohol | 3.0 | 3.0 |
| Microcrystalline wax | 7.0 | 7.0 |
| Ozokerite | 8.0 | 8.0 |
| Antioxidant | 0.05 | 0.05 |

As described above, the solid cosmetic compositions as obtained by the present invention show superior in-use feeling without affecting natural finished appearance, suppresses oil shining, and shows superior moisturizing effect.

What is claimed is:

1. A solid cosmetic composition comprising form 0.1% to 10%, by weight of the composition, of a spherical silica having an average particle size of from 3 to 16 μm wherein said spherical silica is adsorped with moisturizing agent, wherein the moisturizing comprises a compound selected from the group consisting of polyhydric alcohols, mucopolysaccharides, proteins, amino acids and mixtures thereof and wherein the surface of the spherical silica, after being adsorbed with the moisturizing agent, is hydrophobically modified by treating with silicone, the weight ratio of the moisturizing agent to the spherical silica being 1:1 or less.

2. The composition of claim 1 wherein said moisturizing agent is a polyhydric alcohol.

3. The composition of claim 2 wherein said silica adsorped with moisturizing agent is prepared by adsorping a solution of 100 parts by weight of polyhydric alcohol with 10 to 50 parts by weight of water to spherical silica and removing the water.

4. The composition of claim 2 wherein said polyhydric alcohol is glycerin.

5. The composition of claim 4 wherein the weight ratio of spherical silica to glycerin is from 95:5–50:50.

6. The composition of claim 1 wherein said spherical silica, prior to adsorption, has an oil absorbency of 60–500 ml/100 g.

7. A solid cosmetic composition comprising:
   a) form 40% to 99%, by weight of the composition, of a powder component which comprises:
      1) a spherical silica having an average particle size of from 3 to 16 $\mu$m wherein said silica is adsorped with a moisturizing agent, wherein the moisturizing comprises a compound selected from the group consisting of polyhydric alcohols, mucopolysaccharides, proteins, amino acids and mixtures thereof and wherein the surface of the spherical silica, after being adsorbed with the moisturizing agent, is hydrophobically modified by treating with silicone, the weight ration of the moisturizing agent to the spherical silica being 1:1 or less; and
      2) an agglomerate having a particle size of from 100 to 200 $\mu$m made of primary particles of spherical acrylate cross-linked copolymer having an average particle size of not more than 1 $\mu$m; and
   b) from 0.1% to 60%, by weight of the composition, of a binder base; wherein the weight ratio of said spherical silica to said spherical acrylate cross-linked copolymer agglomerate is from 1:9 to 9:1, and wherein the total of said spherical silica and said spherical acrylate cross-linked copolymer agglomerate is from 0.1% to 10%, by weight of the composition.

8. The composition of claim 7 wherein said moisturizing agent is selected from the group consisting of polyhydric alcohols, mucopolysaccharides, amino acids and mixtures thereof.

9. The composition of claim 7 wherein said moisturizing agent is a polyhydric alcohol.

10. The composition of claim 7 wherein said silica adsorbed with moisturizing agent is prepared by adsorping a solution of 100 parts by weight of polyhydric alcohol with 10 to 50 parts by weight of water to spherical silica and removing the water.

11. The composition of claim 7 wherein said moisturizing agent is glycerin.

12. The composition of claim 11 wherein said glycerin-adsorped spherical silica is hydrophobically modified by treating with silicone.

* * * * *